(12) United States Patent
Rodriguez Fernandez et al.

(10) Patent No.: US 9,974,546 B2
(45) Date of Patent: *May 22, 2018

(54) REMOTE TRACTION AND GUIDANCE SYSTEM FOR MINI-INVASIVE SURGERY

(71) Applicant: Levita Magnetics International Corp., San Mateo, CA (US)

(72) Inventors: Manuel Rodriguez Fernandez, Santiago (CL); Alberto Rodriguez Navarro, San Francisco, CA (US)

(73) Assignee: Levita Magnetics International Corp., San Mateo, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/704,828

(22) Filed: May 5, 2015

(65) Prior Publication Data

US 2015/0230801 A1 Aug. 20, 2015

Related U.S. Application Data

(60) Division of application No. 14/337,082, filed on Jul. 21, 2014, now Pat. No. 9,844,391, which is a
(Continued)

(30) Foreign Application Priority Data

Feb. 6, 2009 (CL) .................................... 279-2009

(51) Int. Cl.
*A61B 17/12* (2006.01)
*A61B 17/128* (2006.01)
(Continued)

(52) U.S. Cl.
CPC ...... *A61B 17/1285* (2013.01); *A61B 17/1227* (2013.01); *A61B 17/3423* (2013.01); *A61B 2017/00876* (2013.01)

(58) Field of Classification Search
CPC .......... A61B 17/320092; A61B 5/6884; A61B 17/08; A61B 17/083; A61B 17/122
See application file for complete search history.

(56) References Cited

U.S. PATENT DOCUMENTS 2,863,444 A   12/1958  Winsten
3,146,381 A   8/1964   Louis
(Continued)

FOREIGN PATENT DOCUMENTS

CA   2748471 A1   7/2010
CA   2733465 A1   9/2011
(Continued)

OTHER PUBLICATIONS

International Preliminary Report on Patentability received for PCT Application No. PCT/US2014/018307, dated Sep. 24, 2015, 7 pages.
(Continued)

*Primary Examiner* — Julianna N Harvey
(74) *Attorney, Agent, or Firm* — Cooley LLP

(57) ABSTRACT

A guide and remote traction system for mini-invasive surgery in a body cavity that is easily positioned and hooked and causes lower injury, comprising:
- at least one detachable surgical endoclamp (10) with hooking means (11, 12), assembled with an introduction guide (20) and at an initially open position; and at a naturally closed position when detached from said introduction guide (20) by a detachment mechanism; said endoclamp (10) comprising a portion of ferromagnetic material at the end opposed to said hooking means (11, 12);
- a cylindrically-shaped introduction guide (20) assembled with said detachable surgical endoclamp (10), said introduction guide (20) comprising a mechanism to detach said endoclamp (10); and
(Continued)

at least one remote traction means (30) for said endoc-
lamp (10), acting through the application of an elec-
tromagnetic field over the ferromagnetic portion of said
endoclamp (10).

16 Claims, 6 Drawing Sheets

Related U.S. Application Data continuation of application No. 13/132,185, filed as application No. PCT/IB2009/054307 on Oct. 1, 2009, now Pat. No. 8,790,245.

(51) Int. Cl.
*A61B 17/34* (2006.01)
*A61B 17/122* (2006.01)
*A61B 17/00* (2006.01)

(56) References Cited

U.S. PATENT DOCUMENTS

| | | | |
|---|---|---|---|
| 3,674,014 A | 7/1972 | Tillander | |
| 3,789,285 A | 1/1974 | Nishizawa | |
| 4,364,377 A | 12/1982 | Smith | |
| 4,380,999 A | 4/1983 | Healy | |
| 4,971,067 A | 11/1990 | Bolduc et al. | |
| 4,976,723 A | 12/1990 | Schad | |
| 5,282,806 A | 2/1994 | Haber et al. | |
| 5,304,183 A | 4/1994 | Gourlay et al. | |
| 5,304,185 A | 4/1994 | Taylor | |
| 5,307,805 A | 5/1994 | Byrne | |
| 5,415,160 A | 5/1995 | Ortiz et al. | |
| 5,449,361 A | 9/1995 | Preissman | |
| 5,450,842 A | 9/1995 | Tovey et al. | |
| 5,458,603 A | 10/1995 | Futch, Sr. | |
| 5,458,693 A | 10/1995 | Codorniu | |
| 5,465,711 A | 11/1995 | Moll et al. | |
| 5,496,317 A | 3/1996 | Goble et al. | |
| 5,499,986 A | 3/1996 | Dimarco | |
| 5,529,568 A | 6/1996 | Rayman | |
| 5,593,379 A | 1/1997 | Rayman | |
| 5,595,562 A | 1/1997 | Grier | |
| 5,654,864 A | 8/1997 | Ritter et al. | |
| 5,665,100 A | 9/1997 | Yoon | |
| 5,681,260 A | 10/1997 | Ueda et al. | |
| 5,728,121 A | 3/1998 | Bimbo et al. | |
| 5,733,292 A | 3/1998 | Gustilo et al. | |
| 5,749,881 A | 5/1998 | Sackier et al. | |
| 5,766,189 A | 6/1998 | Matsuno | |
| 5,782,748 A | 7/1998 | Palmer et al. | |
| 5,797,911 A | 8/1998 | Sherman et al. | |
| 5,849,015 A | 12/1998 | Haywood et al. | |
| 5,893,873 A | 4/1999 | Rader et al. | |
| 6,015,414 A | 1/2000 | Werp et al. | |
| 6,099,537 A | 8/2000 | Sugai et al. | |
| 6,099,550 A | 8/2000 | Yoon | |
| 6,123,657 A | 9/2000 | Ishikawa et al. | |
| 6,126,647 A | 10/2000 | Posey et al. | |
| 6,173,715 B1 | 1/2001 | Sinanan et al. | |
| 6,212,419 B1 | 4/2001 | Blume et al. | |
| 6,216,028 B1 | 4/2001 | Haynor et al. | |
| 6,241,671 B1 | 6/2001 | Ritter et al. | |
| 6,311,082 B1 | 10/2001 | Creighton, IV et al. | |
| 6,315,709 B1 | 11/2001 | Garibaldi et al. | |
| 6,330,467 B1 | 12/2001 | Creighton, IV et al. | |
| 6,340,365 B2 | 1/2002 | Dittrich et al. | |
| 6,358,196 B1 * | 3/2002 | Rayman | A61B 17/00234 600/12 |
| 6,398,791 B1 | 6/2002 | Que et al. | |
| 6,399,146 B1 | 6/2002 | Harris et al. | |
| 6,401,723 B1 | 6/2002 | Garibaldi et al. | |
| 6,440,133 B1 | 8/2002 | Beale et al. | |
| 6,459,924 B1 | 10/2002 | Creighton, IV et al. | |
| 6,464,710 B1 | 10/2002 | Foster | |
| 6,488,615 B1 | 12/2002 | Mitchiner et al. | |
| 6,523,919 B1 | 2/2003 | Israelsen et al. | |
| 6,537,196 B1 | 3/2003 | Creighton, IV et al. | |
| 6,594,517 B1 | 7/2003 | Nevo | |
| 6,630,879 B1 | 10/2003 | Creighton, IV et al. | |
| 6,656,199 B1 | 12/2003 | Lafontaine | |
| 6,677,752 B1 | 1/2004 | Creighton, IV et al. | |
| 6,689,119 B1 | 2/2004 | Di Caprio et al. | |
| 6,705,989 B2 | 3/2004 | Cuschieri et al. | |
| 6,719,765 B2 | 4/2004 | Bonutti | |
| 6,761,681 B2 | 7/2004 | Schmid et al. | |
| 6,817,364 B2 | 11/2004 | Garibaldi et al. | |
| 6,824,511 B1 | 11/2004 | Bell et al. | |
| 6,916,314 B2 | 7/2005 | Schneider et al. | |
| 7,017,584 B2 | 3/2006 | Garibaldi et al. | |
| 7,094,245 B2 | 8/2006 | Adams et al. | |
| 7,169,104 B2 | 1/2007 | Ueda et al. | |
| 7,182,089 B2 | 2/2007 | Ries | |
| 7,182,775 B2 | 2/2007 | De Guillebon et al. | |
| 7,264,584 B2 | 9/2007 | Ritter et al. | |
| 7,311,107 B2 | 12/2007 | Harel et al. | |
| 7,313,429 B2 | 12/2007 | Creighton, IV et al. | |
| 7,341,063 B2 | 3/2008 | Garbibaldi et al. | |
| 7,344,553 B2 | 3/2008 | Opolski et al. | |
| 7,416,335 B2 | 8/2008 | Munger | |
| 7,429,259 B2 | 9/2008 | Cadeddu et al. | |
| 7,431,726 B2 | 10/2008 | Spence et al. | |
| 7,686,827 B2 | 3/2010 | Hushka | |
| 7,691,103 B2 | 4/2010 | Fernandez et al. | |
| 7,708,756 B2 | 5/2010 | Nobis et al. | |
| 7,736,356 B2 | 6/2010 | Cooper et al. | |
| 7,766,810 B2 | 8/2010 | Ohdaira | |
| 7,769,427 B2 | 8/2010 | Shachar | |
| 7,772,950 B2 | 8/2010 | Tunay | |
| 7,774,046 B2 | 8/2010 | Werp et al. | |
| 7,780,054 B2 | 8/2010 | Wales | |
| 7,799,050 B2 | 9/2010 | Hensley et al. | |
| 7,837,612 B2 | 11/2010 | Gill et al. | |
| 7,850,591 B2 | 12/2010 | Spector | |
| 7,963,903 B2 | 6/2011 | Ghiron et al. | |
| 7,966,059 B2 | 6/2011 | Creighton, IV et al. | |
| 8,038,612 B2 | 10/2011 | Paz | |
| 8,043,290 B2 | 10/2011 | Harrison et al. | |
| 8,057,472 B2 | 11/2011 | Walker et al. | |
| 8,060,184 B2 | 11/2011 | Hastings et al. | |
| 8,066,715 B2 | 11/2011 | Ducharme | |
| 8,082,035 B2 | 12/2011 | Glukhovsky | |
| 8,133,254 B2 | 3/2012 | Dumbauld et al. | |
| 8,136,888 B2 | 3/2012 | Suzuki et al. | |
| 8,137,268 B2 | 3/2012 | Van Lue | |
| 8,157,149 B2 | 4/2012 | Olson et al. | |
| 8,187,286 B2 | 5/2012 | Jugenheimer et al. | |
| 8,197,494 B2 | 6/2012 | Jaggi et al. | |
| 8,235,272 B2 | 8/2012 | Nicholas et al. | |
| 8,241,322 B2 | 8/2012 | Whitman et al. | |
| 8,246,529 B2 | 8/2012 | Riehl et al. | |
| 8,252,021 B2 | 8/2012 | Boulnois et al. | |
| 8,267,854 B2 | 9/2012 | Asada et al. | |
| 8,301,226 B2 | 10/2012 | Csavoy et al. | |
| 8,303,495 B2 | 11/2012 | Ducharme | |
| 8,313,497 B2 | 11/2012 | Walberg et al. | |
| 8,316,861 B2 | 11/2012 | Brewer et al. | |
| 8,316,862 B2 | 11/2012 | Shapiro et al. | |
| 8,333,695 B2 | 12/2012 | Cuschieri | |
| 8,360,972 B2 | 1/2013 | Paz | |
| 8,364,277 B2 | 1/2013 | Glukhovsky | |
| 8,377,044 B2 | 2/2013 | Coe et al. | |
| 8,382,754 B2 | 2/2013 | Odom et al. | |
| 8,480,668 B2 | 7/2013 | Fernandez et al. | |
| 8,491,626 B2 | 7/2013 | Roy et al. | |
| 8,517,931 B2 | 8/2013 | Minnelli et al. | |
| 8,518,057 B2 | 8/2013 | Walberg et al. | |
| 8,556,919 B2 | 10/2013 | Aguirre et al. | |
| 8,579,787 B2 | 11/2013 | Shapiro et al. | |
| 8,585,685 B2 | 11/2013 | Hagg | |
| 8,602,981 B2 | 12/2013 | Deutch | |
| 8,608,773 B2 | 12/2013 | Tierney et al. | |

(56) References Cited

U.S. PATENT DOCUMENTS

| | | | |
|---|---|---|---|
| 8,623,011 B2 | 1/2014 | Spivey | |
| 8,628,529 B2 | 1/2014 | Aldridge et al. | |
| 8,636,762 B2 | 1/2014 | Whitman et al. | |
| 8,637,818 B2 | 1/2014 | Balakin | |
| 8,685,043 B2 | 4/2014 | Jugenheimer et al. | |
| 8,758,394 B2 | 6/2014 | Zimmerling et al. | |
| 8,764,769 B1 | 7/2014 | Rodriguez-Navarro et al. | |
| 8,790,245 B2* | 7/2014 | Rodriguez Fernandez | A61B 17/3421 600/106 |
| 8,820,602 B2 | 9/2014 | Walberg et al. | |
| 8,827,891 B2 | 9/2014 | Roberts | |
| 8,894,574 B2 | 11/2014 | Ellman | |
| 8,926,656 B2 | 1/2015 | Palermo et al. | |
| 8,968,356 B2 | 3/2015 | Mueller | |
| 9,011,468 B2 | 4/2015 | Ketai et al. | |
| 9,339,285 B2 | 5/2016 | Rodriguez-Navarro et al. | |
| 9,844,391 B2 | 12/2017 | Rodriguez Fernandez et al. | |
| 2002/0100486 A1 | 8/2002 | Creighton, IV et al. | |
| 2003/0114731 A1 | 6/2003 | Cadeddu et al. | |
| 2003/0125752 A1 | 7/2003 | Werp et al. | |
| 2003/0208185 A1 | 11/2003 | Sheffer et al. | |
| 2004/0050395 A1 | 3/2004 | Ueda et al. | |
| 2004/0064153 A1 | 4/2004 | Creighton, IV et al. | |
| 2004/0230100 A1 | 11/2004 | Shluzas | |
| 2004/0249262 A1 | 12/2004 | Werp et al. | |
| 2005/0080440 A1* | 4/2005 | Durgin et al. | 606/157 |
| 2005/0131390 A1 | 6/2005 | Heinrich et al. | |
| 2005/0165449 A1 | 7/2005 | Cadeddu et al. | |
| 2005/0220583 A1 | 10/2005 | Lutz | |
| 2005/0250988 A1 | 11/2005 | Ewers et al. | |
| 2006/0015178 A1* | 1/2006 | Moaddeb et al. | 623/2.36 |
| 2006/0074448 A1 | 4/2006 | Harrison et al. | |
| 2006/0079897 A1* | 4/2006 | Harrison et al. | 606/61 |
| 2006/0089633 A1 | 4/2006 | Bleich et al. | |
| 2006/0149135 A1 | 7/2006 | Paz | |
| 2006/0152309 A1 | 7/2006 | Mintchev et al. | |
| 2006/0228421 A1 | 10/2006 | Seeney et al. | |
| 2006/0241691 A1 | 10/2006 | Wilk | |
| 2006/0247522 A1 | 11/2006 | Mcgee | |
| 2006/0293566 A1 | 12/2006 | Brown | |
| 2007/0016010 A1 | 1/2007 | Creighton, IV et al. | |
| 2007/0027458 A1 | 2/2007 | Sixto, Jr. et al. | |
| 2007/0043359 A1 | 2/2007 | Altarac et al. | |
| 2007/0073102 A1 | 3/2007 | Matsuno et al. | |
| 2007/0135678 A1 | 6/2007 | Suzuki | |
| 2007/0135802 A1 | 6/2007 | Suzuki | |
| 2007/0255273 A1 | 11/2007 | Fernandez et al. | |
| 2007/0270629 A1 | 11/2007 | Charles | |
| 2008/0097496 A1 | 4/2008 | Chang et al. | |
| 2008/0108860 A1 | 5/2008 | Bell et al. | |
| 2008/0134474 A1 | 6/2008 | Uryasov | |
| 2008/0171907 A1 | 7/2008 | Long et al. | |
| 2008/0243106 A1 | 10/2008 | Coe et al. | |
| 2008/0249534 A1 | 10/2008 | Gruber et al. | |
| 2008/0269779 A1 | 10/2008 | Cadeddu et al. | |
| 2009/0005636 A1 | 1/2009 | Pang et al. | |
| 2009/0043246 A1* | 2/2009 | Dominguez | A61B 17/0218 604/21 |
| 2009/0062772 A1 | 3/2009 | Wakeford et al. | |
| 2009/0192344 A1 | 7/2009 | Bakos et al. | |
| 2009/0267717 A1 | 10/2009 | Baskett | |
| 2010/0036394 A1 | 2/2010 | Mintz et al. | |
| 2010/0036399 A1 | 2/2010 | Viola | |
| 2010/0081876 A1 | 4/2010 | Linenkugel et al. | |
| 2010/0105984 A1 | 4/2010 | Brewer et al. | |
| 2010/0113872 A1 | 5/2010 | Asada et al. | |
| 2010/0114126 A1 | 5/2010 | Neff | |
| 2010/0145147 A1 | 6/2010 | Pinsky et al. | |
| 2010/0160739 A1 | 6/2010 | Van Lue | |
| 2010/0168523 A1 | 7/2010 | Ducharme | |
| 2010/0174234 A1 | 7/2010 | Werp et al. | |
| 2010/0193566 A1 | 8/2010 | Scheib et al. | |
| 2010/0204727 A1 | 8/2010 | Dominguez | |
| 2010/0217245 A1 | 8/2010 | Prescott | |
| 2010/0268254 A1* | 10/2010 | Golden | A61B 17/122 606/142 |
| 2010/0298645 A1 | 11/2010 | Deutch | |
| 2011/0040152 A1 | 2/2011 | Kim et al. | |
| 2011/0054306 A1 | 3/2011 | Del Nido et al. | |
| 2011/0087223 A1 | 4/2011 | Spivey | |
| 2011/0087224 A1 | 4/2011 | Cadeddu et al. | |
| 2011/0087249 A1 | 4/2011 | Rodrigues et al. | |
| 2011/0105848 A1 | 5/2011 | Sadovsky et al. | |
| 2011/0121050 A1 | 5/2011 | Nicholas et al. | |
| 2011/0130787 A1 | 6/2011 | Cinquin et al. | |
| 2011/0184440 A1 | 7/2011 | Saldinger | |
| 2011/0230726 A1 | 9/2011 | Viola | |
| 2011/0276941 A1 | 11/2011 | Oi | |
| 2011/0283822 A1 | 11/2011 | Cadeddu et al. | |
| 2011/0284014 A1 | 11/2011 | Cadeddu et al. | |
| 2011/0285488 A1 | 11/2011 | Scott et al. | |
| 2011/0295067 A1 | 12/2011 | Rodriguez Fernandez et al. | |
| 2011/0313415 A1 | 12/2011 | Fernandez et al. | |
| 2012/0016362 A1 | 1/2012 | Heinrich et al. | |
| 2012/0035416 A1 | 2/2012 | Fernandez et al. | |
| 2012/0065627 A1 | 3/2012 | Ghabrial et al. | |
| 2012/0078292 A1 | 3/2012 | Banju | |
| 2012/0085358 A1 | 4/2012 | Cadeddu et al. | |
| 2012/0101488 A1 | 4/2012 | Aldridge et al. | |
| 2013/0030462 A1 | 1/2013 | Keating et al. | |
| 2013/0085341 A1 | 4/2013 | Nobis et al. | |
| 2013/0110128 A1 | 5/2013 | Schostek et al. | |
| 2013/0123828 A1 | 5/2013 | Culmer et al. | |
| 2013/0158523 A1 | 6/2013 | Bergs et al. | |
| 2013/0158659 A1 | 6/2013 | Bergs et al. | |
| 2013/0158660 A1 | 6/2013 | Bergs et al. | |
| 2013/0226226 A1 | 8/2013 | Garrison et al. | |
| 2013/0245356 A1 | 9/2013 | Fernandez et al. | |
| 2013/0253275 A1 | 9/2013 | Ransden et al. | |
| 2013/0289768 A1 | 10/2013 | Yeung et al. | |
| 2014/0243586 A1 | 8/2014 | Rohaninejad et al. | |
| 2014/0257370 A1 | 9/2014 | Taylor et al. | |
| 2014/0276941 A1 | 9/2014 | Rodriguez-Navarro et al. | |
| 2014/0277104 A1 | 9/2014 | Rodriguez-Navarro et al. | |
| 2014/0336470 A1 | 11/2014 | Rodriguez Fernandez et al. | |
| 2014/0350574 A1 | 11/2014 | Farritor et al. | |
| 2016/0228138 A1 | 8/2016 | Rodriguez-Navarro et al. | |
| 2016/0302811 A1 | 10/2016 | Rodriguez-Navarro et al. | |

FOREIGN PATENT DOCUMENTS

| | | |
|---|---|---|
| CN | 2244381 Y | 1/1997 |
| CN | 101090672 A | 12/2007 |
| CN | 201079412 Y | 7/2008 |
| CN | 201091596 Y | 7/2008 |
| CN | 101534725 A | 9/2009 |
| CN | 102068288 A | 5/2011 |
| CN | 102355865 A | 2/2012 |
| DE | 4212430 A1 | 10/1993 |
| DE | 19534618 A1 | 3/1997 |
| DE | 102005006705 A1 | 8/2006 |
| EP | 1797823 A1 | 6/2007 |
| EP | 1972284 A2 | 9/2008 |
| EP | 2366357 A1 | 9/2011 |
| EP | 2391277 A1 | 12/2011 |
| EP | 1942810 B1 | 8/2012 |
| EP | 2595548 A1 | 5/2013 |
| JP | 09-192137 A | 7/1997 |
| JP | 2005-021576 A | 1/2005 |
| JP | 4320214 B2 | 8/2009 |
| JP | 2009-538699 A | 11/2009 |
| WO | WO-2005/004734 A1 | 1/2005 |
| WO | WO-2006/071120 A1 | 7/2006 |
| WO | WO-2007/142977 A2 | 12/2007 |
| WO | WO-2007/142977 A3 | 12/2007 |
| WO | WO-2008/039237 A1 | 4/2008 |
| WO | 2008/131128 A1 | 10/2008 |
| WO | 2009/019288 A2 | 2/2009 |
| WO | 2009/070743 A1 | 6/2009 |
| WO | WO-2010/089635 A1 | 8/2010 |
| WO | 2011/091483 A1 | 8/2011 |
| WO | 2012/010910 A1 | 1/2012 |
| WO | WO-2014/159023 A1 | 10/2014 |

(56) References Cited

FOREIGN PATENT DOCUMENTS

| WO | WO-2014/163872 A1 | 10/2014 |
|----|-------------------|---------|
| WO | 2015/112645 A1    | 7/2015  |
| WO | WO-2016/168380 A1 | 10/2016 |

OTHER PUBLICATIONS

International Preliminary Report on Patentability received for PCT Application No. PCT/US2014/021537, dated Sep. 24, 2015, 7 pages.
International Search Report & Written Opinion received for PCT Patent Application No. PCT/US2014/021537, dated Jul. 30, 2014, 8 pages.
International Search Report and Written Opinion received for PCT Patent Application No. PCT/US2015/012319, dated May 4, 2015, 8 pages.
Non-Final Office Action received for U.S. Appl. No. 13/132,185, dated May 21, 2013, 18 pages.
Notice of Allowance received for U.S. Appl. No. 13/132,185, dated Mar. 14, 2014, 7 pages.
Non Final Office Action received for U.S. Appl. No. 14/337,082, dated Jul. 13, 2015, 10 pages.
Domínguez, Guillermo M., "Colecistectomía con un trócar asistida por imanes de neodimio. Reporte de un caso", Asociación Mexicana de Cirugía Endoscópica, vol. 8, No. 4, Abstract provided, Oct.-Dec. 2007, pp. 172-176.
International Preliminary Report on Patentability received for International application No. PCT/IB2009/054307, completed on Mar. 30, 2011, 29 pages (6 pages of English Translation and 23 pages of IPRP).
International Search Report received for PCT Patent Application No. PCT/IB2009/054307, dated Feb. 8, 2010, 9 pages (4 pages of English Translation and 5 pages of Search Report).
International Written Opinion received for PCT Patent Application No. PCT/IB2009/054307, dated Feb. 8, 2010, 8 pages.
International Search Report and Written Opinion received for PCT Patent Application No. PCT/US2014/018307, dated Jul. 18, 2014, 10 pages.
Invitation to Pay Additional fees received for PCT Patent Application No. PCT/US2014/018307, dated May 5, 2014, 2 pages.
Non-Final Office Action received for U.S. Appl. No. 14/200,302, dated May 25, 2016, 12 pages.
Notice of Allowance received for U.S. Appl. No. 14/019,404, dated Apr. 5, 2016, 3 pages.
Notice of Allowance received for U.S. Appl. No. 14/019,404, dated Mar. 14, 2016, 7 pages.
Advisory Action received for U.S. Appl. No. 14/337,082, dated Apr. 15, 2016, 3 pages.
Final Office Action received for U.S. Appl. No. 14/337,082, dated Jan. 25, 2016, 9 pages.
Extended European Search Report dated Jul. 20, 2016, for EP Application No. 14 778 895.4, filed on Feb. 25, 2014, 7 pages.
Final Office Action dated Dec. 28, 2016, for U.S. Appl. No. 14/200,302, filed on Mar. 7, 2014, 15 pages.
International Search Report dated May 4, 2015, for PCT Application No. PCT/US2015/012319, filed on Jan. 21, 2015, 2 pages.
International Search Report dated Aug. 22, 2016, for PCT Application No. PCT/US2016/027390, filed on Apr. 13, 2016, 4 pages.
Non-Final Office Action dated Jul. 21, 2016, for U.S. Appl. No. 14/337,082, filed Jul. 21, 2014, 9 pages.
Non-Final Office Action dated Oct. 24, 2013, for U.S. Appl. No. 14/019,370, filed Sep. 5, 2013, 7 pages.
Non-Final Office Action dated Oct. 22, 2015, for U.S. Appl. No. 14/019,404, filed Sep. 5, 2013, 6 pages.
Notice of Allowance dated Feb. 14, 2014, for U.S. Appl. No. 14/019,370, filed Sep. 5, 2013, 7 pages.
Notice of Allowance dated Mar. 14, 2014, for U.S. Appl. No. 13/132,185, filed Aug. 17, 2011, 7 pages.
Wikipedia (2015). "Stainless Steel," retrieved from https://en.wikipedia.org/wiki/Stainless_steel, 13 pages.
Written Opinion of the International Searching Authority dated May 4, 2015, for PCT Application No. PCT/US2015/012319, filed on Jan. 21, 2015, 5 pages.
Written Opinion of the International Searching Authority dated Aug. 22, 2016, for PCT Application No. PCT/US2016/027390, filed on Apr. 13, 2016, 9 pages.
Extended European Search Report dated Dec. 20, 2016, for EP Application No. 09 839 564.3, filed on Oct. 1, 2009, 11 pages.
Extended European Search Report dated Sep. 27, 2017, for EP Application No. 15 741 055.6, filed on Jan. 21, 2015, 9 pages.
Final Office Action dated Sep. 6, 2017, for U.S. Appl. No. 14/200,302, filed Mar. 7, 2014, 9 pages.
Non-Final Office Action dated May 22, 2017, for U.S. Appl. No. 14/200,302, filed Mar. 7, 2014, 14 pages.
Non-Final Office Action dated Jul. 24, 2017, for U.S. Appl. No. 15/098,262, filed Apr. 13, 2016, 9 pages.
Notice of Allowance dated May 3, 2017, for U.S. Appl. No. 14/337,082, filed Jul. 21, 2014, 7 pages.
Notice of Allowance dated Aug. 25, 2017, for U.S. Appl. No. 14/337,082, filed Jul. 21, 2014, 7 pages.
Notice of Allowance dated Nov. 22, 2017, for U.S. Appl. No. 14/200,302, filed Mar. 7, 2014, 5 pages.

* cited by examiner

PREVIOUS ART

REMOTE TRACTION AND GUIDANCE SYSTEM FOR MINI-INVASIVE SURGERY

CROSS-REFERENCE TO RELATED APPLICATIONS

This application is a divisional of U.S. patent application Ser. No. 14/337,082, filed Jul. 21, 2014, now issued as U.S. Pat. No. 9,844,391, which is a continuation of U.S. patent application Ser. No. 13/132,185, having a 371(c) date of Aug. 17, 2011, now U.S. Pat. No. 8,790,245, which is a National Stage Application of PCT/IB2009/054307, filed on Oct. 1, 2009, which claims the benefit of Patent Application Serial No. 279-2009, filed Feb. 6, 2009, in Chile, all of which are hereby incorporated by reference in their entirety.

FIELD OF THE INVENTION

The present invention is directed to a guide and remote traction system for mini-invasive surgery or endocavitary surgery, said system being easily maneuvered, positioned, hooked and used, which diminishes the number of required incisions to perform surgical procedures. In particular, the present invention consists in a guide and remote traction system for mini-invasive surgery or endocavitary surgery that is easily positioned and hooked, comprising: a detachable surgical endoclamp; a detachable and self-closing introduction guide assembled together with said surgical endoclamp; and remote magnetic traction means for said endoclamp.

BACKGROUND OF THE INVENTION

Surgery is under constant change and development. Currently, surgical procedures and technologies are oriented to carry out surgeries that cause the lowest possible injury to the patient. The applied concept is to achieve advantages for the individual, such as lower pain, lower post-surgery recovery periods, shortened hospitalization, lower complications associated to the procedure and better cosmetic results, which results in a better life quality for the patient and savings for health insurance systems. With this inspiration, endoscopic or minimally invasive surgery has been developed, which allows carrying out surgical interventions through small incisions in the patient, hence avoiding larger incisions and the higher metabolic costs of open surgery.

A solution to this need is disclosed in U.S. Pat. No. 7,169,104, published on Mar. 18, 2004, which discloses a remote guide anchoring system including an hooking device that is hooked to a body part in a patient's body; a magnetic clamp made of a magnetic material that is connected to the hooking device; and a magnetic device located outside of the patient's body to guide the clamp, which produces a magnetic field to move said magnetic clamp. As can be seen in this document and its figures, the invention in this document requires a second clamp to close the magnetic clamp or to hook the clamp to the anchoring system. The former solution refers to a solution for digestive endoscopy that is very difficult to apply in laparoscopic surgery since the assembly solution for the clamp and its traction system is very difficult to carry out inside cavities.

Technical Problem

These surgery techniques need entrance points into the individual, which requires performing a total wall incision and generally inserting a working trocar (or port). Through these entrances, necessary elements are introduced, both optical (cameras for internal visualization) and surgical tools, e.g. clamps, electroscalpel, scissors, etc. In this type of surgery, it is necessary to detach and raise adjacent organs or tissues for a cleaner and more effective surgery result. Usually, this detachment and rising is performed by using clamps or hooking means, which are directly manipulated from the outside through a working port.

These working ports are the incision points that must be performed in the body wall of the individual, with the risks and complications associated to a total thickness body wall incision, mainly: important post-surgery pain, intra- and post-surgery bleeding risk, infection risk and risk of developing subsequent hernias. All these complications decrease the life quality of the patient and increase health insurance costs. Additionally, there is also an important aesthetical issue, since these incisions necessarily leave a subsequent scar as a sequel. Due to this, it is necessary to use the minimal possible number of incisions to perform the desired surgical procedure, therefore decreasing intra- and post-surgery complications and hence getting the best post-surgery results.

Solution to Problem

The present invention solves the problem of positioning and effectively hooking an endoclamp to an organ or tissue to be pulled, making the assembly easy to use, since it comprises a self-closing endoclamp actuated from the introduction guide. Subsequently, this endoclamp is moved by applying a magnetic force through the body wall using the remote traction means.

Advantageous Effects of Invention

The present invention has been realized, consisting in a guide and remote traction system for mini-invasive surgery with easy positioning and hooking and lower injury since it makes possible to eliminate one or several incisions performed with the previous art techniques, which brings about a benefit for patients. This allows a significant reduction on the recovery time of patients, removing potential risks associated to incisions and avoiding undesirable scars. Furthermore, the present invention proposes a guide and remote traction system comprising a hooking mechanism to the organ or tissue to be treated that is easily and safely operated, which facilitates its use by physicians. Therefore, the present invention is beneficial, since it decreases the number of incisions to perform the surgery and is easily used. The present invention solves a problem of positioning and effective hooking to the organ to be pulled, allowing an easy use and performing surgery with lower injury to the patient.

PREFERRED EMBODIMENT OF THE INVENTION

The present invention consists in a guide and remote traction system for mini-invasive surgery in a body cavity that is easily positioned and hooked and causes lower injury, comprising:
at least one endoclamp with surgical hooking means, assembled with a guide and at an initially open position; and at a naturally closed position when detached from said guide by the detachment mechanism; said endoclamp comprising a portion of ferromagnetic material at the end opposed to said hooking means;
a cylindrically-shaped introduction guide assembled with said detachable surgical endoclamp, said guide comprising a mechanism to detach said endoclamp;
at least one remote traction means for said at least one endoclamp, acting through the application of an electromagnetic field over the ferromagnetic portion of said endoclamp from outside of said body cavity.

Figure 1:
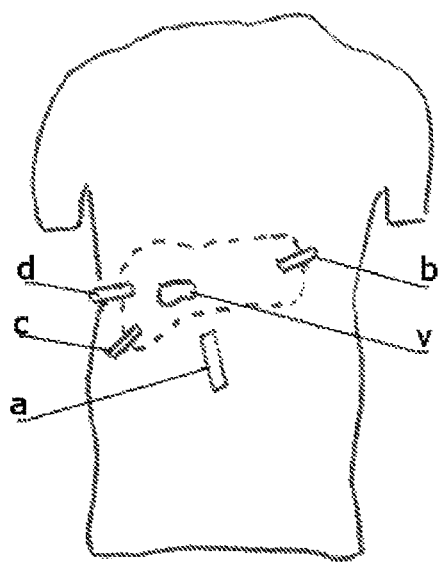
FIG. 1 is a schematic view of a mini-invasive surgery, particularly a laparoscopic cholecystectomy, according to the previous art.

As observed in FIG. 1, a mini-invasive laparoscopic-like surgery is performed by techniques of the prior art in which, in this case, 4 incisions are practiced in the abdominal wall to place the trocars, wherein 1 trocar (a) is used for insertion of an endoscopic camera, and 3 trocars (b, c and d) are used to rise, manipulate and section the organ to be treated, e.g. the gall bladder (v), with hooking means such as conventional laparoscopic clamps.

Figure 2:
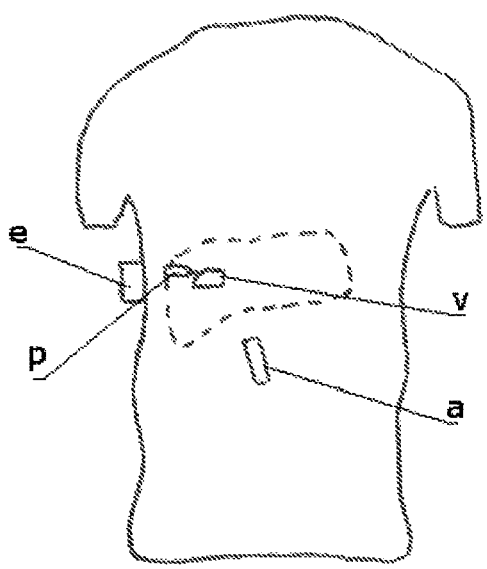
FIG. 2 is a schematic view of a mini-invasive surgery with the guide system with remote traction according to the present invention. A decrease in the number of access points can be observed.

Instead, FIG. 2 shows a mini-invasive surgery using the guide system and remote traction according to the present invention; wherein it can be appreciated that only one incision is carried out in the abdominal wall for only one trocar (a), through which one or more clamps (p) are introduced, which are driven by one or more magnets or electromagnets (e) to manipulate the organ (v); the endoscopic camera to visualize the mini-invasive surgery is introduced through this same trocar, as well as an element to dissect and subsequently extract the tissue or organ.

Figure 3:
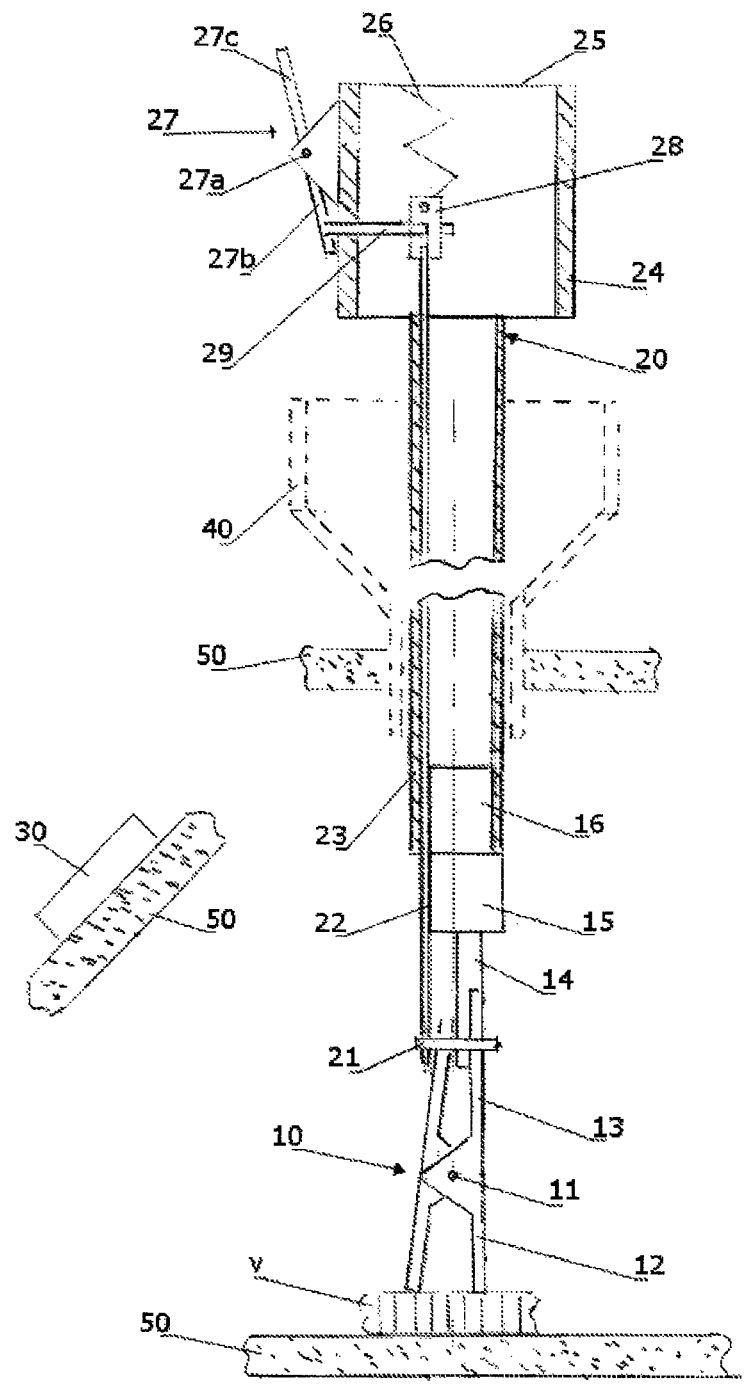
FIG. 3 is a schematic view of the guide system and remote traction according to the present invention in an initial configuration comprising an introduction guide and an assembled open clamp.

As illustrated in FIG. 3, the guide and remote traction system for mini-invasive surgery in a body cavity that is easily positioned and hooked and causes lower injury, comprises: an introduction guide (20) assembled with a detachable surgical endoclamp (10) and a remote traction means (30) of said endoclamp (10) to move said endoclamp by applying a magnetic field over an end of said clamp from the outside of said body cavity, e.g. an electromagnet.

Said endoclamp (10) comprises two separate pieces substantially at its center and rotatable about an axis (11), each of said separate pieces defining a hooking end (12) and a handling end (13) with a radial spring (not shown in the Figures) that holds the endoclamp (10) in its naturally closed position. A first handling end (13) is joined to a projection (14) coupled to a cylindrical butt means (15) with a diameter wider than projection (14), and said butt means (15) extends to an anchoring means (16) introduced inside the guide (20); wherein the butt means (15) and anchoring means (16) comprise a portion made of a ferromagnetic material, e.g. iron, nickel, cobalt, iron oxides, etc.

Said detachment mechanism of said introduction guide (20) comprises a securing ring (21) joined to a first end of a substantially rod-like connecting piece (22), said connecting piece (22) passing through the inside of a guide tube (23), said guide tube (23) connecting at one end to the anchoring means (16) of the endoclamp (10) and at the other end to a detaching set (24) to detach said endoclamp (10); said connection piece (22) is joined at its second end to an unlocking piece (28) connected to a tensioned spring (26) fixed to the rear wall (25) of the detaching set (24); said unlocking piece (28) having a perforation with a pin (29) passing therethrough. Said pin (29) is fixed at its end to an actuator (27) that is rotatable around a central axis (27a) that defines an operative end (27b) and an actuator end (27c).

In an initial position, said rotatable actuator (27) is in a first position with the operative end (27b) closer to the unlocking set (24) than the actuator end (27c), which is far away from the unlocking set (24); the pin (29) passes through the perforation of the unlocking piece (28) and the unlocking piece is located at a distance from the rear wall (25) longer than the natural spring length (26) in such a way as to hold the spring in tension in its first position. In this initial position, the connecting piece (22) holds the securing ring (21) around and joining the handling ends (13) in such a way as to hold the endoclamp (10) open, i.e. with separated hooking ends (12).

Figure 4:
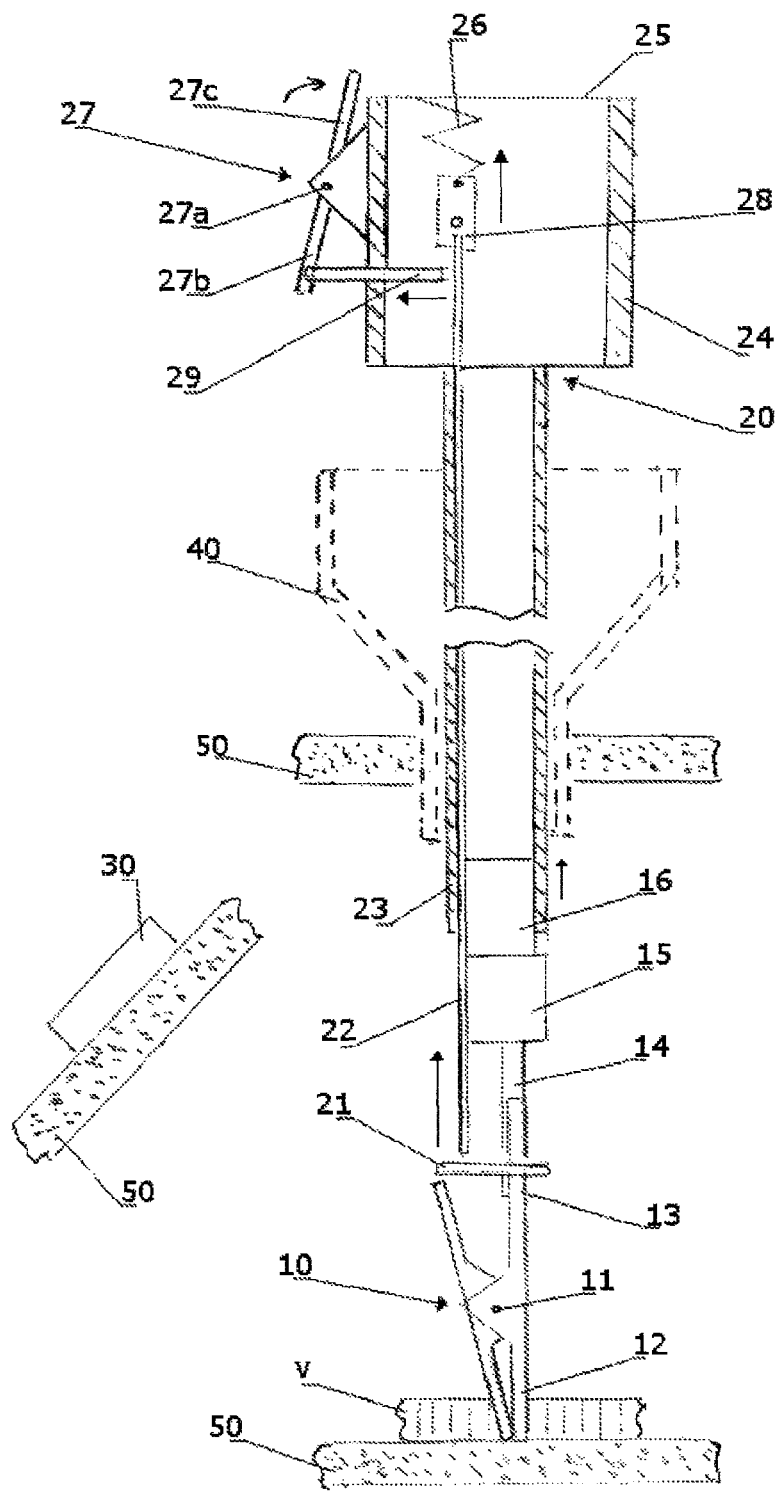
FIG. 4 is another schematic view of the guide system and remote traction according to the present invention in a detachment position with a closed clamp.

When introducing the introduction guide (20) assembled with the endoclamp (10) through a trocar installed in a body cavity subjected to mini-invasive surgery, the introduction guide (20) and the endoclamp (10) can be guided, introduced and alignedly actuated through said trocar. When the endoclamp (10) is in its initial position, the endoclamp is open and is directed toward the organ or tissue (v) to be treated. When the endoclamp (10) is correctly placed at the organ or tissue (v), the endoclamp is put into a, unlock position, shown in FIG. 4, which is achieved by pressing the actuator end (27c) as to remove the pin (29) from the perforation of the unlocking piece (28); in this way, the restriction imposed on the spring (26) is released and the spring returns to its natural position, bringing together the unlocking piece (28) and the rear wall (25), and removing the securing ring (21) from the endoclamp (10) by means of the connection piece (22). In turn, the endoclamp (10) is released into its natural position, and the hooking ends (12) are closed, thus trapping the organ or tissue (v).

Figure 5:
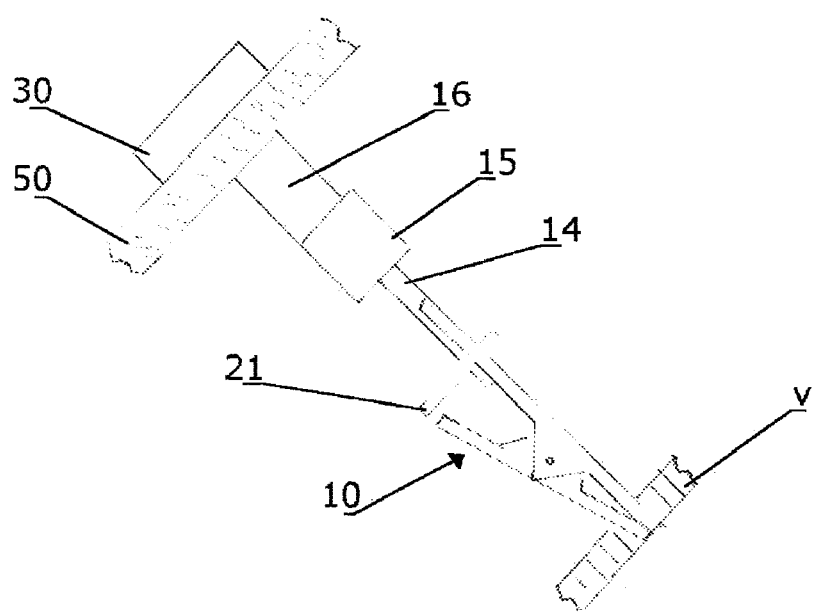
FIG. 5 is a schematic view of the endoclamp detached from the introduction guide in traction operative position.

As shown in FIG. 5, when the endoclamp (10) is fixed to the organ or tissue (v), the introduction guide (20) is removed from the trocar and it can be used to introduce another element into the body cavity; furthermore, the endoclamp (10) is brought close to the body cavity wall (50) near the remote traction means (30) and the magnetic field is activated in such a way as to make said endoclamp (10) to be attracted by said remote traction means (30) and orienting its butt means (15) and the hooking means (16) toward the inner side of the body cavity wall (50). In this way, the remote traction means (30) can guide and position the endoclamp (10) remotely from the outside of the body cavity.

Then, in the aforementioned way, an organ or tissue in a body cavity can be manipulated with one or more endoclamps by repeating the described procedure. The organ remains located in an optimal position to carry out the corresponding surgical intervention with only one incision to install a single trocar.

Said one or more endoclamps remain fixed at their position or can be moved along the body cavity, thanks to one or several remote traction means of said endoclamp by applying an electromagnetic field over the ferromagnetic portion of said endoclamp from the outside of said body cavity.

Preferably, said remote traction means generates an electromagnetic field with a magnetic induction ranging from 0.1 to 1 Tesla (1,000 to 10,000 Gauss) in the surroundings of said traction means, to generate a force ranging from 2.94 to 4.9 N (300 and 500 grams) over the endoclamp according to the present invention at a distance ranging from 10 to 30 mm of the abdominal wall; reaching a body wall width of up to 80 mm in case of obesity. For this end, said remote traction means comprises a permanent magnet such as, e.g. a magnetized steel or Alnico (alloy comprising 24% by weight of cobalt, 8% by weight of aluminum, 14% by weight of nickel, 51% by weight of iron and 3% by weight of copper) or ferrite (80% by weight of iron oxide and 20% by weight of strontium oxide) magnet.

More preferably, said traction means comprises a rare earth mineral magnet, e.g.: $RE-M_5$- and $RE_2M_{17}$-type, wherein "RE" is samarium (Sm), promethium (Pr) and neodymium (Nd) and "M" is a mixture of cobalt (Co) with metals such as iron (Fe), copper (Cu), zirconium (Zr), titanium (Ti), hafnium (Hf) and manganese (Mn); e.g. $SmCo_5$ made by GE Research Lab in Schenectady, Nueva York (EEUU), or "neodymium-iron-boron", $Nd_2Fe_{14}B$, developed in 1983 by Sumitomo (Japan) and General Motors (EEUU).

EMBODIMENT OF THE INVENTION

According to another preferred embodiment of the invention, said remote traction means can comprise an electromagnet and a voltage regulator to vary the magnetic induction generated by varying the voltage on the electromagnet. Preferably, said electromagnet generates an electromagnetic field with a magnetic induction ranging from 0.1 to 1 Tesla (1,000 to 10,000 Gauss) in the surroundings of said traction means, to generate the required force over the endoclamp according to the present invention at a distance ranging from 10 to 30 mm.

According to another preferred embodiment of the invention, said remote traction means can comprise an electromagnet and an electric current regulator to vary the generated magnetic induction by varying the electric current intensity over the electromagnet, said magnetic induction ranging from 0.1 to 1 Tesla (1,000 to 10,000 Gauss) according to the present invention.

According to an embodiment of the present invention, said electromagnet can comprise a paramagnetic material core that comprises one or several of the following materials: air, aluminum, magnesium, titanium, ferric chloride and tungsten.

According to another embodiment of the present invention, said electromagnet can comprise a ferromagnetic material core that comprises one or several of the following materials: iron, nickel, cobalt, aluminum, iron-silicon or alnico and permalloy alloys, this latter comprising 20% by weight of steel and 80% by weight of nickel.

Figure 6:
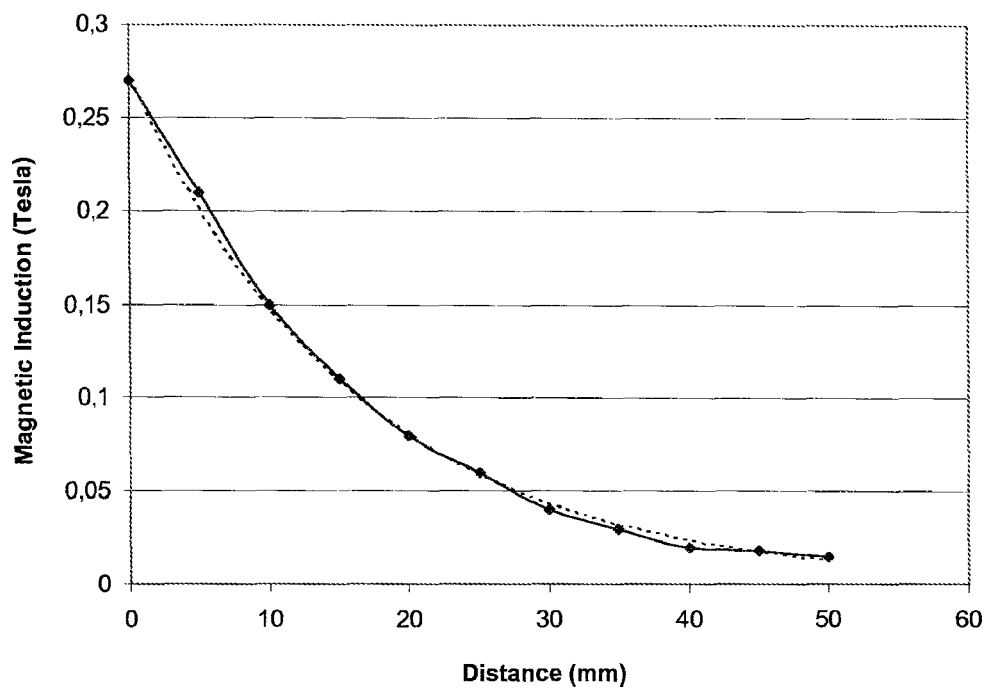
FIG. 6 shows a plot of magnetic field density as a function of distance generated by a remote traction means according to the present invention.
Figure 7:
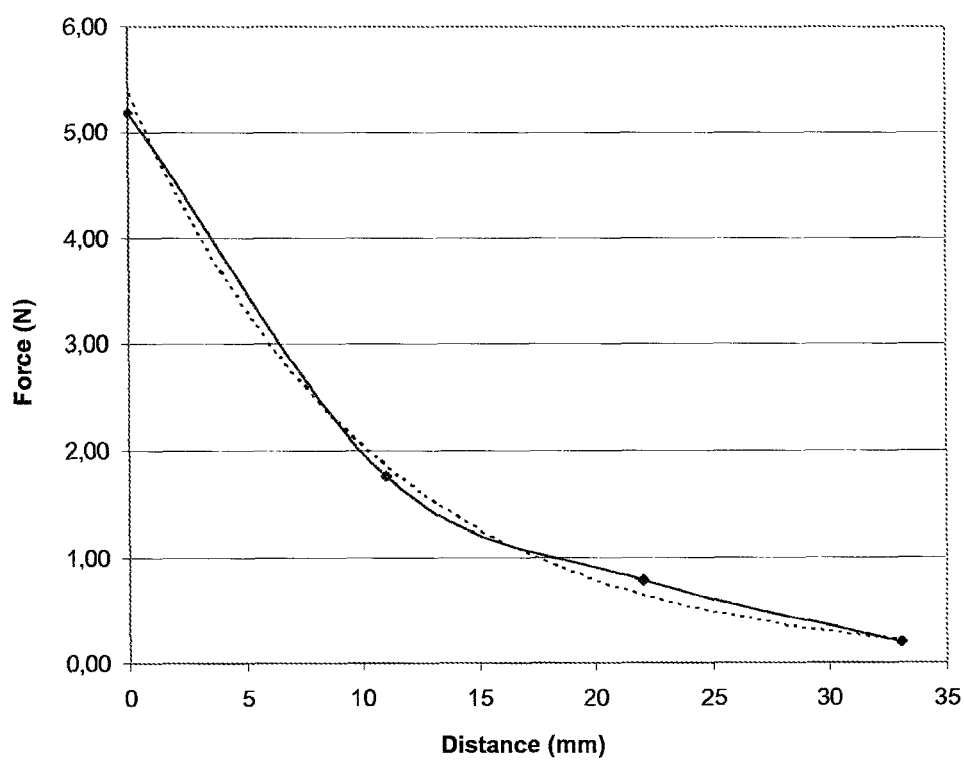
FIG. 7 shows a plot of magnetic field force as a function of distance generated by said remote traction means over an endoclamp according to the present invention.

In a first example of the present invention, FIG. 6 shows a plot of magnetic field density as a function of distance generated by a remote traction means according to the present invention which comprises a rare earth magnet. FIG. 7 shows a plot of magnetic field force as a function of distance generated by said remote traction means over an endoclamp according to the present invention. From FIG. 7, a characteristic magnet curve can be interpolated using equation: (a) $F=5.3757e^{-0.0967}$; with a quadratic fit with $R^2=0.9897$, being F the force (in N) generated over the endoclamp and d the distance (in mm) between the remote traction means and the endoclamp; a magnet with these characteristics can generate 1.76 N (180 grams) at a distance of 11 mm according to the width requirements of the body cavity and the organ to be manipulated with the endoclamp of this first example.

According to the thickness of the patient's body cavity and the weight of the organ to be manipulated, in a second example a 2.94 N (300 grams) can be required to maintain and manipulate an organ through a body cavity of 20 mm. Thanks to FIG. 7 and equation (a), a new characteristic curve can be easily interpolated: $2.94=5.3757e^{-0.0967*20}+B$; therefore $B=2.1628$; and the resulting equation is: (b) $F=5.3757e^{-0.0967*d}+2.1628$; wherein for a 0 mm distance, said magnet must generate a force of 7.5385 N (739 grams) over said endoclamp.

Figure 8:
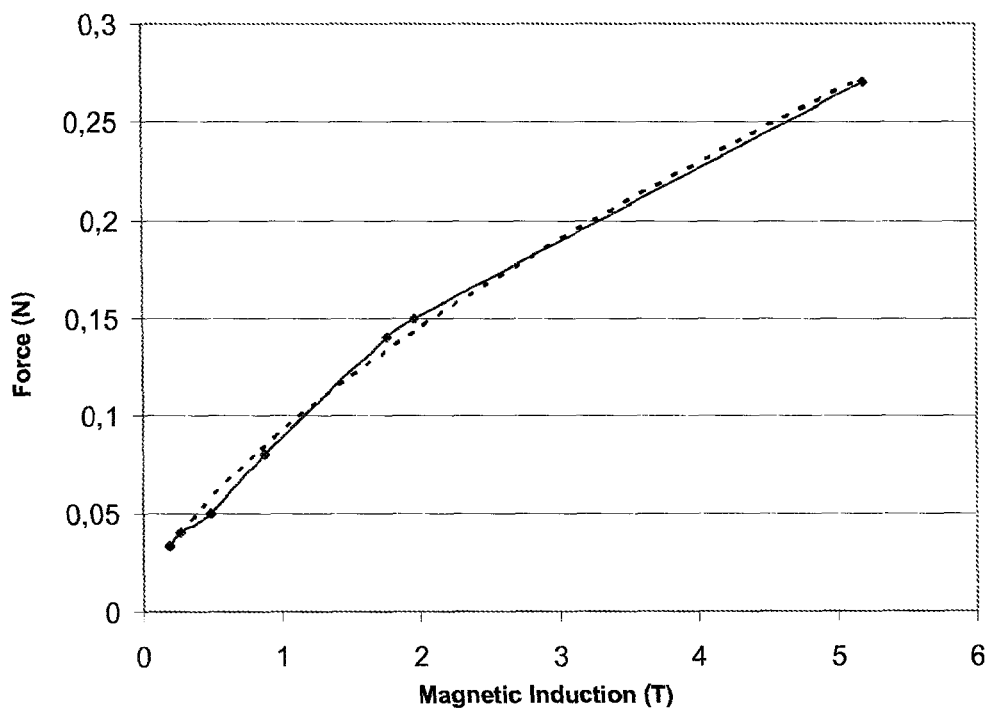
FIG. 8 shows a plot relating the magnetic induction of a traction means with a rare earth magnet with the force generated over an endoclamp by said magnetic induction, said traction means and said endoclamp according to the present invention.

FIG. 8 shows a plot relating the magnetic induction of a rare earth magnet with the force generated over the endoclamp according to the present invention, with the equation: (c) $B=0.0917*F^{0.66}$; with a quadratic fit with $R^2=0.9915$, wherein F is the force in Newtons and B is the magnetic induction in Teslas; for this second example, the magnet required for the remote traction means according to the present invention should be dimensioned for a magnetic induction of 0.3478 Teslas (3478 Gauss).

Figure 9:
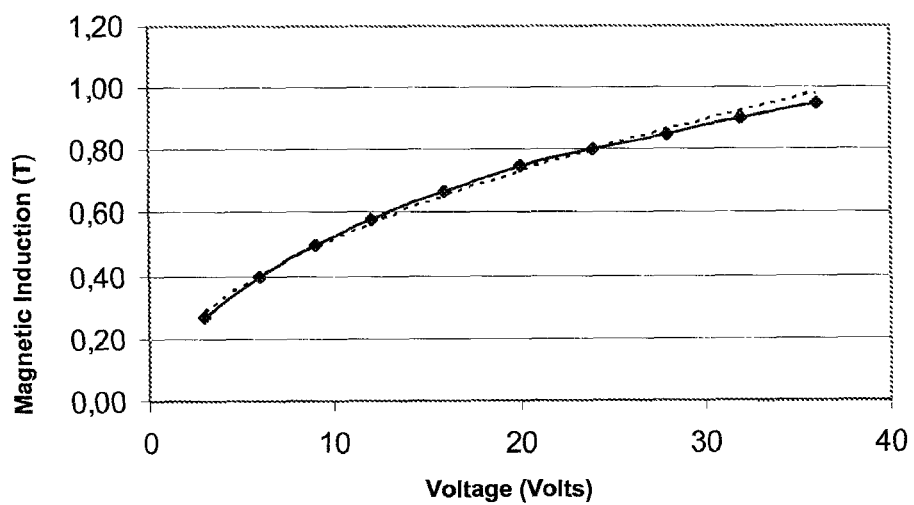
FIG. 9 shows a plot of magnetic induction as a function of voltage over an electromagnet of a traction means according to the present invention.

According to another preferred embodiment of the invention, said remote traction means can comprise an electromagnet and a voltage regulator to vary the magnetic induction generated by varying the voltage on the electromagnet. FIG. 9 shows a plot of magnetic induction as a function of voltage over an electromagnet with a 2 A current I; a path length of 8.3 cm; a spire number of 4.245; and a cold-laminated steel core with a diameter of 10 mm and permeability 1.99. Said plot of FIG. 9 allows obtaining a characteristic electromagnet curve represented by equation: (d) $B=0.1621*V^{0.5018}$; with a quadratic fit having $R^2=0.9956$, wherein B is the magnetic induction in Teslas at a distance of 0 mm from the electromagnet and V is the voltage in Volts applied over said electromagnet.

For the aforementioned example, where a 2.94 N (300 grams) force must be generated over the endoclamp according to the present invention through a body wall of 20 mm, a magnetic induction of 0.3478 Teslas (3478 Gauss) should be produced at a distance of 0 mm; therefore, according to the plot in FIG. 9 and using equation (d), the required voltage is $V=(0.3478/0.1621)^{1/0.5918}=4.58$ Volts. Hence, the voltage regulator of said traction means must be regulated to get the deduced 4.58 Volts voltage. In this way, the traction means that comprises an electromagnet with a voltage regulator or a current regulator can be adjusted to apply the minimal necessary force over the endoclamp to hold it firmly at its position against the body cavity without applying an excessive force that could damage the tissues and other organs of the body cavity under surgery.

INDUSTRIAL APPLICABILITY

The present invention has industrial applicability in the manufacturing industry of mini-invasive surgery or endocavitary surgery tools. The present invention is especially useful in videolaparoscopic cholecystectomy, but is not limited to this procedure.

The invention claimed is:

1. A system for traction of tissue, comprising:
a clamp comprising a first piece and a second piece, each piece defining an end for engaging tissue and a handling end; and
an introduction guide comprising an actuator and a detachment mechanism longitudinally slidable within the introduction guide,
wherein the handling end of the first piece of the clamp is detachably attachable to the introduction guide and comprises a portion made of ferromagnetic material, wherein the ferromagnetic material is configured to be at least partially held within the introduction guide, wherein the actuator is configured to retract the detachment mechanism away from the clamp to both release the clamp from the introduction guide and fix the clamp to tissue, and wherein the clamp is spring-biased toward a closed position.

2. The system of claim 1, wherein the clamp is movable between an open position and the closed position, and wherein the actuator is configured to move the clamp between the open and closed positions.

3. The system of claim 2, wherein the first piece and second piece of the clamp are rotatable relative to an axis between the open and closed positions.

4. The system of claim 1, wherein the handling end of the second piece of the clamp is rotatable relative to an axis, and the detachment mechanism comprises a rod held against the handling end of the second piece of the clamp when the introduction guide is assembled with the clamp.

5. The system of claim 1, wherein the actuator comprises an actuator end, the actuator end configured to move toward the clamp to retract the detachment mechanism away from the clamp.

6. The system of claim 1, wherein a predetermined amount of retraction of the detachment mechanism both fixes and releases the clamp.

7. A system for traction of tissue, comprising:
an introduction guide comprising a detachment mechanism longitudinally slidable within the introduction guide, wherein a distal end of the introduction guide comprises a tube;
a clamp having open and closed positions, wherein the clamp is detachably attachable to the introduction guide; and
a remote traction means to position the clamp remotely from outside the body cavity,
wherein the introduction guide comprises an actuator configured to move the clamp between the open and closed positions, wherein the actuator is further configured to retract the detachment mechanism away from the clamp to both release the clamp from the introduction guide and fix the clamp to tissue, and wherein the clamp is spring-biased toward the closed position.

8. The system of claim 7, wherein the clamp comprises a ferromagnetic material, and wherein the remote traction means comprises a magnet.

9. The system of claim 8, wherein a magnetic field generated by the remote traction means is adjustable.

10. The system of claim 7, wherein the clamp comprises a first piece and a second piece, each piece defining an end for engaging tissue and a handling end, wherein the handling end of the first piece of the clamp is detachably attachable to the introduction guide.

11. The system of claim 10, wherein the handling end of the first piece of the clamp comprises a portion made of ferromagnetic material.

12. The system of claim 10, wherein the first piece and second piece of the clamp are rotatable relative to an axis between the open and closed positions.

13. The system of claim 7, wherein a magnetic field generated by the remote traction means is between 1,000 G to 10,000 G at about the remote traction means.

14. The system of claim 7, wherein the clamp comprises a first end for engaging tissue, a second end opposite the first end, and a projection coupled therebetween, wherein the detachment mechanism comprises a rod extending longitudinally out of the introduction guide, the rod held against the first end of the clamp when the introduction guide is assembled with the clamp.

15. The system of claim 7, wherein the actuator comprises an actuator end, the actuator end configured to move toward the clamp to retract the detachment mechanism away from the clamp.

16. The system of claim 7, wherein a predetermined amount of retraction of the detachment mechanism both fixes and releases the clamp.

* * * * *